(12) United States Patent
DiLoreto et al.

(10) Patent No.: US 11,865,002 B2
(45) Date of Patent: Jan. 9, 2024

(54) PUMP ASSEMBLY FOR A PENILE PROSTHESIS

(71) Applicant: Boston Scientific Scimed, Inc., Maple Grove, MN (US)

(72) Inventors: Mark Edward DiLoreto, Chaska, MN (US); James Ryan Mujwid, Hudson, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 481 days.

(21) Appl. No.: 16/949,705

(22) Filed: Nov. 11, 2020

(65) Prior Publication Data
US 2021/0145585 A1 May 20, 2021

Related U.S. Application Data

(60) Provisional application No. 62/936,904, filed on Nov. 18, 2019.

(51) Int. Cl.
*A61F 2/26* (2006.01)

(52) U.S. Cl.
CPC ........ *A61F 2/26* (2013.01); *A61F 2250/0003* (2013.01); *A61F 2250/0013* (2013.01)

(58) Field of Classification Search
CPC ............................ A61F 2/26; A61F 2250/0013
See application file for complete search history.

(56) References Cited

U.S. PATENT DOCUMENTS

| | | | |
|---|---|---|---|
| 5,141,509 A | 8/1992 | Burton et al. | |
| 7,244,227 B2 | 7/2007 | Morningstar et al. | |
| 8,241,203 B2 | 8/2012 | Fogarty | |
| 8,257,246 B1 * | 9/2012 | Fogarty | A61F 2/26 600/40 |
| 11,311,382 B2 * | 4/2022 | Mujwid | A61F 2/26 |
| 2002/0082471 A1 * | 6/2002 | Henkel | A61F 2/26 600/39 |
| 2002/0082472 A1 * | 6/2002 | Derus | A61F 2/26 600/40 |
| 2014/0179995 A1 | 6/2014 | Fogarty et al. | |

(Continued)

FOREIGN PATENT DOCUMENTS

WO 2011057642 A1 5/2011

OTHER PUBLICATIONS

International Search Report and Written Opinion for PCT Application No. PCT/US2020/070774, dated Feb. 11, 2021, 11 pages.

*Primary Examiner* — Samuel G Gilbert
(74) *Attorney, Agent, or Firm* — Brake Hughes Bellermann LLP

(57) ABSTRACT

According to an aspect, an inflatable penile prosthesis includes a fluid reservoir configured to hold fluid, an inflatable member, and a pump assembly configured to transfer the fluid between the fluid reservoir and the inflatable member. The pump assembly includes a pump bulb, a valve body, a valve disposed within the valve body, a first fluid port configured to be fluidly coupled to the fluid reservoir, and a second fluid port configured to be fluidly coupled to the inflatable member. The valve is configured to move between an inflation position and a deflation position. The valve includes a first member and second member, the first member being configured to move with respect to the second member.

16 Claims, 14 Drawing Sheets

(56) References Cited

U.S. PATENT DOCUMENTS

| | | | |
|---|---|---|---|
| 2016/0015519 A1* | 1/2016 | Henkel | A61F 2/26 600/40 |
| 2018/0042724 A1 | 2/2018 | Diloreto | |
| 2019/0307567 A1 | 10/2019 | Mujwid et al. | |

* cited by examiner

PUMP ASSEMBLY FOR A PENILE PROSTHESIS

CROSS-REFERENCE TO RELATED APPLICATION

This application claims priority to U.S. Provisional Patent Application No. 62/936,904, filed on Nov. 18, 2019, entitled "PUMP ASSEMBLY FOR A PENILE PROSTHESIS", the disclosure of which is incorporated by reference herein in its entirety.

TECHNICAL FIELD

This disclosure relates generally to bodily implants and more specifically to bodily implants, such as a penile prosthesis that includes a pump.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism pulls fluid from a fluid reservoir and then transfers the fluid to the inflatable members. The pump mechanism may include a pump bulb and a valve body that includes one or more valve components. According to some existing designs of inflatable penile prostheses, the complexity of the valve components may cause the pump bulb to get struck in a collapsed state or otherwise function improperly.

SUMMARY

According to an aspect, an inflatable penile prosthesis includes a fluid reservoir configured to hold fluid, an inflatable member, and a pump assembly configured to transfer the fluid between the fluid reservoir and the inflatable member. The pump assembly includes a pump bulb, a valve body, a valve disposed within the valve body, a first fluid port configured to be fluidly coupled to the fluid reservoir, and a second fluid port configured to be fluidly coupled to the inflatable member. The valve is configured to move between an inflation position and a deflation position. The valve includes a first member and second member, the first member being configured to move with respect to the second member.

In some embodiments, the second member of the valve is fixedly coupled within the valve body. In some embodiments, the first member of the valve defines a cavity, the second member of the valve includes a projection, the cavity of the first member being configured to receive the projection of the second member. In some embodiments, the first member of the valve defines a cavity, the second member of the valve includes a projection, the cavity of the first member being configured to receive the projection of the second member, the second member being fixedly coupled within the valve body.

In some embodiments, the valve includes a third member. In some embodiments, the valve includes a third member, the third member includes a surface configured to engage a surface of the first member of the valve. In some embodiments, the valve includes a third member, the third member includes a surface configured to engage a surface of the first member of the valve, the surface of the third member being a curved surface, the surface of the first member being a curved surface. In some embodiments, the valve includes a third member, the third member includes a convex surface configured to engage a concave surface of the first member of the valve.

In some embodiments, the first member of the valve defines a cavity, the valve incudes a third member, the third member includes a projection that is configured to be at least partially disposed within the cavity of the first member. In some embodiments, the first member of the valve defines a cavity, the valve incudes a third member, the third member includes a projection that is configured to be at least partially disposed within the cavity of the first member, the second member of the valve being fixedly coupled within the valve body.

In some embodiments, the inflatable penile prosthesis includes a biasing member disposed between the first member and the second member. In some embodiments, the biasing member is a spring or a spring member.

In some embodiments, the valve body includes a sealing ring, the first member of the valve includes a surface, the surface being configured to engage the sealing ring when the valve is in the deflation position.

In some embodiments, the first member of the valve includes a contact ring, the second member of the valve includes a projection having an outer surface, the contact ring being configured to engage the outer surface of the projection. In some embodiments, the valve body includes a retainer member configured to engage the second member of the valve to help fixedly couple the second member of the valve to the valve body.

According to an aspect, an inflatable penile prosthesis includes a fluid reservoir configured to hold fluid; an inflatable member; and a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, wherein the valve includes a first member and second member, the first member being configured to move with respect to the second member, the valve member includes a biasing member disposed between a portion of the valve body and the first member of the valve.

In some embodiments, the biasing member is a spring.

In some embodiments, the first member of the valve includes a surface that is configured to engage a surface of the second member of the valve. In some embodiments, the first member of the valve includes a convex surface that is configured to engage a surface of the second member of the valve. In some embodiments, the valve body includes a sealing ring, the first member of the valve includes a surface, the surface being configured to engage the sealing ring when the valve is in the deflation position.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
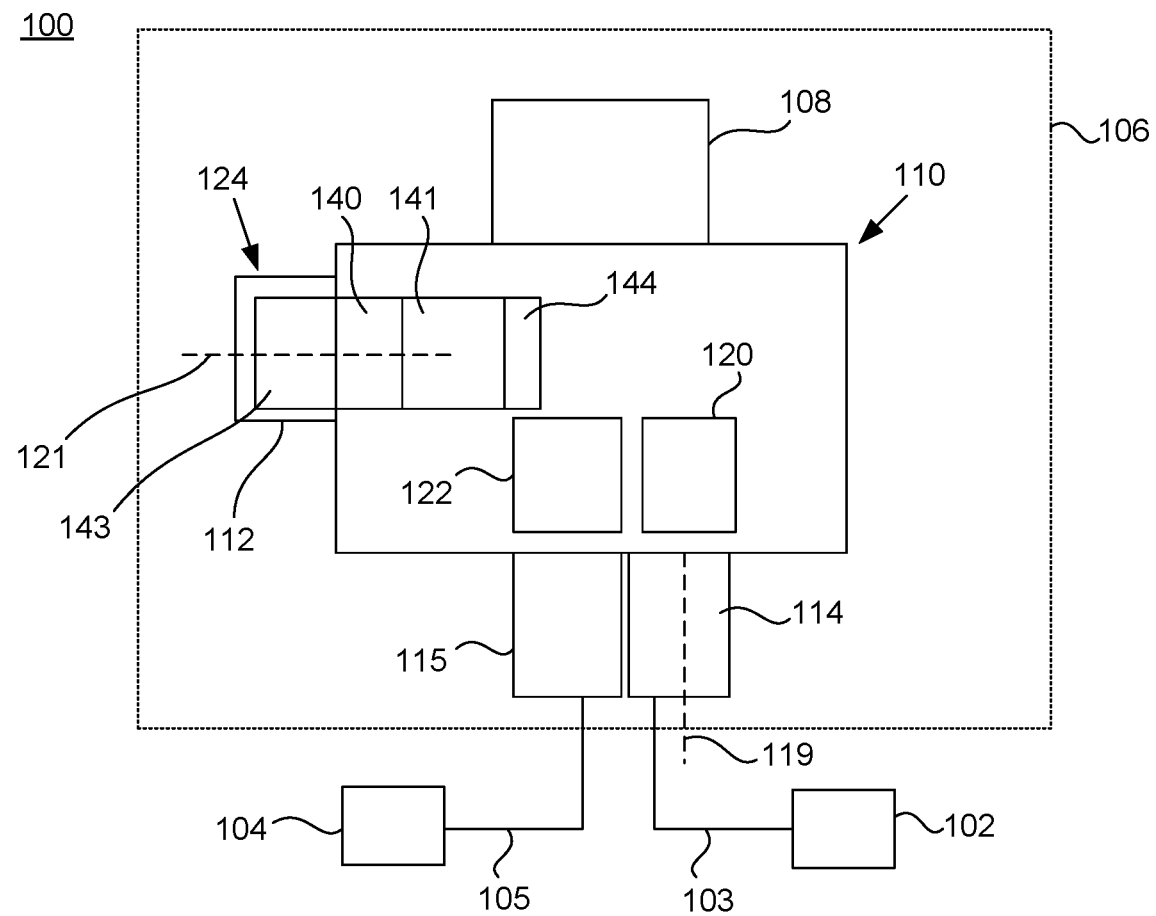
FIG. 1 schematically illustrates an inflatable penile prosthesis according to an aspect.

FIG. 1 illustrates an inflatable penile prosthesis 100 including a fluid reservoir 102, an inflatable member 104, and a pump assembly 106 configured to transfer fluid between the fluid reservoir 102 and the inflatable member 104 according to an aspect. The inflatable member 104 may be implanted into the corpus cavernosae of the user, the fluid reservoir 102 may be implanted in the abdomen or pelvic cavity of the user (e.g., the fluid reservoir 102 may be implanted in the lower portion of the user's abdominal cavity or the upper portion of the user's pelvic cavity), and the pump assembly 106 may be implanted in the scrotum of the user.

The pump assembly 106 includes a pump bulb 108, a valve body 110, a push valve 124 movably coupled to the valve body 110, a first fluid port 114 fluidly coupled to the fluid reservoir 102 (via a first conduit connector 103), and a second fluid port 115 fluidly coupled to the inflatable member 104 (via a second conduit connector 105). The first fluid port 114 and the second fluid port 115 may extend from an end portion of the valve body 110. In some examples, the fluid transfer ports are disposed on (or defined by) a tube adaptor (e.g., a triple tube adaptor) that is separate from the valve body 110, and the tube adaptor is coupled to the valve body 110. In some examples, the first fluid port 114 includes an elongated tubular member defining a cavity. In some examples, the second fluid port 115 includes two separate elongated tubular members (e.g., one tubular member being fluidly coupled to a first cylinder member of the inflatable member 104 and another tubular member being fluidly coupled to a second cylinder member of the inflatable member 104).

The push valve 124 is configured to move from an inflation position to a deflation position along an axis 121 within a bore of the valve body 110 when pressed by a user in order to control the direction of the fluid through the fluid passageways of the valve body 110. The push valve 124 includes a movable valve element 140 and a biasing member 144 that biases the movable valve element 140 to the inflation position. In some examples, the movable valve element 140 is configured to move to the deflation position in a linear direction based on a single instantaneous push of the movable valve element 140 by a user. The pump assembly 106 includes a button component 112 that encloses a portion of the movable valve element 140 when the movable valve element 140 is in the inflation position. The button component 112 may be a flexible button-shaped material that extends over the movable valve element 140.

In some examples, the movable valve element 140 includes a directional control valve. In some examples, the movable valve element 140 includes one or more ring members (e.g., annular rings or retainer rings). In some examples, the biasing member 144 includes a spring.

In some embodiments, the valve or the movable valve element 140 includes more than one piece or member. In the illustrated embodiment, the valve or movable valve element 140 includes a first member 141 and a second member 143. The first member 141 is movable with respect to the second member 143. In other embodiments, the valve or movable valve element 140 includes more than two members.

The design of the push valve 124 may reduce (or eliminate) the possibility for the pump bulb 108 to get stuck in a collapsed state even if the first squeeze to switch from the deflation mode to the inflation mode does not successfully move the movable valve element 140 to the inflation position. When the movable valve element 140 is in the inflation position, the inflatable penile prosthesis 100 is in an inflation mode (or inflation cycle). When the movable valve element 140 is in the deflation position, the inflatable penile prosthesis 100 is in a deflation mode (or deflation cycle). In some examples, a single, instantaneous push of the movable valve element 140 transfers the inflatable penile prosthesis 100 to the deflation position (e.g., as opposed to pressing and holding the movable valve element 140 for a certain predetermined time). In some examples, movement of the movable valve element 140 to the deflation position causes a fluid pathway to open between the second fluid port 115 and the first fluid port 114 such that fluid can be transferred from the inflatable member 104 to the fluid reservoir 102 via the pump assembly 106 in a manner that bypasses the pump bulb 108.

In contrast, in the inflation mode, the pump bulb 108 is used to transfer fluid from the fluid reservoir 102 to the inflatable member 104. For example, the user may depress (or squeeze) the pump bulb 108 and then release the pump bulb 108, and then repeat these operations until the desired rigidity is achieved in the inflatable member 104. The release of the pump bulb 108 creates a suction force that pulls fluid from the fluid reservoir 102 to the pump bulb 108, and the depression of the pump bulb 108 expels the fluid from the pump bulb 108 to the inflatable member 104. In some examples, in the inflation mode, the valve body 110 provides an optimized fluid passageway via the push valve 124 that may decrease the pressure drop across the push valve 124 for faster inflate time and/or decrease the fluid resistance thereby requiring less pump bulb squeeze force to inflate.

The pump bulb 108 may be a flexible member defining a cavity. The pump bulb 108 is coupled to and extends from the valve body 110. In some examples, the pump bulb 108 extends from the valve body 110 in a direction that is opposite to the direction in which the first fluid port 114 and the second fluid port 115 extend from the valve body 110 (e.g., located on opposite ends of the valve body 110). The pump bulb 108 may be a squeeze pump. In some examples, the pump bulb 108 includes ribbing or dimples to aid the user in gripping the pump bulb 108. As indicated above, the pump bulb 108 may use suction and pressure to move the fluid in and out of the cavity of the pump bulb 108 in the inflation mode. For example, the user may depress or squeeze the pump bulb 108 to expel the fluid out of the cavity, and, when the flexible member returns to its original shape, the resulting suction pushes the fluid into the cavity of the pump bulb 108. In some examples, the pump bulb 108 may have a bulb spring rate that is designed to refill the pump bulb 108 in a selected time frame.

The valve body 110 defines one or more fluid passageways through the valve body 110. The valve body 110 includes valve components disposed within the fluid passageways to control the flow of the fluid through the valve body 110 in the inflation mode and the deflation mode. In some examples, the valve body 110 includes a block of material that defines the fluid passageways and encloses the valve components. In some examples, the valve body 110 includes a silicone material. In some examples, the valve body 110 may be molded from a silicone material having a medium durometer value. In some examples, the pump assembly 106 includes an outer protective casing that is disposed over the valve body 110. In some examples, the outer protective casing has a material (e.g., a polymer material) that is different from the valve body 110. In some examples, the outer protective casing includes one or more tactile features that help the user locate the valve body 110 (in order to locate the push valve 124). In some examples, the tactile features include protruded portions, ridges, grooves, bumps, and/or depressions.

The valve body 110 includes a refill valve 120 and an inflation valve 122. In some examples, the valve body 110 includes an anti-auto inflate valve. The refill valve 120 may be used when the pump bulb 108 is refilled. The refill valve 120 is not used in the deflation mode. In some examples, the refill valve 120 is a one-way valve. In some examples, the refill valve 120 is disposed in a fluid passageway within the valve body 110 between the first fluid port 114 and the pump bulb 108. In some examples, the fluid passageway having the refill valve 120 that extends between the first fluid port 114 and the pump bulb 108 is used only for refilling the pump bulb 108 (e.g., a separated fluid pathway), which may decrease bulb refill time (e.g., deceases the wait time between squeezes). In some examples, the refill valve 120 is fluidly coupled to the bore (where the push valve 124 moves within) and the pump bulb 108.

In some examples, the refill valve 120 is aligned with the first fluid port 114. For example, the refill valve 120 may have an inlet and an outlet, where fluid enters the inlet from the first fluid port 114 and exits the outlet to the pump bulb 108. The first fluid port 114 may define a longitudinal axis 119 that extends along the fluid pathway (e.g., between the inlet and the outlet) of the refill valve 120. In some examples, the longitudinal axis 119 is orthogonal to the axis 121. The alignment of the refill valve 120 with the first fluid port 114 may minimize fluid pathway tortuosity, and/or decrease pressure drop across the refill valve 120. In some examples, the refill valve 120 includes a floating check ball with fluting (which may increase or maximize fluid velocity across the refill valve 120). In some examples, the refill valve 120 includes a biasing member that biases the refill valve 120 to a sealing position. In some examples, the biasing member includes a spring. In some examples, the refill valve 120 does not include a biasing member.

The inflation valve 122 may be disposed within a fluid passageway between the pump bulb 108 and the push valve 124. The inflation valve 122 may be used during the inflation of the inflatable member 104 (e.g., when the fluid is transferred from the pump bulb 108 to the inflatable member 104). The inflation valve 122 is not used during the deflation mode. In some examples, the inflation valve 122 is a one-way valve. In some examples, the inflation valve 122 includes a check ball and a biasing member. The biasing member may bias the check ball to a sealing position. In some examples, the biasing member includes a spring.

In the inflation position (and when the user is operating the pump bulb 108), the fluid may flow from the first fluid port 114 (from the fluid reservoir 102) to the pump bulb 108 via the refill valve 120, and from the pump bulb 108 to the second fluid port 115 via the inflation valve 122 and the push valve 124 (and then to the inflatable member 104). In response to the movable valve element 140 being pressed to the deflation position, the position in the movable valve element 140 within the bore of the valve body 110 may open a fluid passageway in the valve body 110 to transfer fluid from the inflatable member 104 to the fluid reservoir 102 that bypasses the pump bulb 108. For example, the movable valve element 140, when moved to the deflation position, is configured to change the fluid passageway through the bore to transfer fluid from the second fluid port 115 to the first fluid port 114 such that the pump bulb 108 is bypassed. In some examples, due to the pressure inside of the inflatable member 104, some of the fluid may be automatically transferred from the inflation member 104 to the fluid reservoir 102 via the pump assembly 106, and then the user may squeeze the inflatable member 104 to transfer some of the remaining fluid in the inflatable member 104.

Each of the first conduit connector 103 and the second conduit connector 105 may define a lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 50 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

Figure 2:
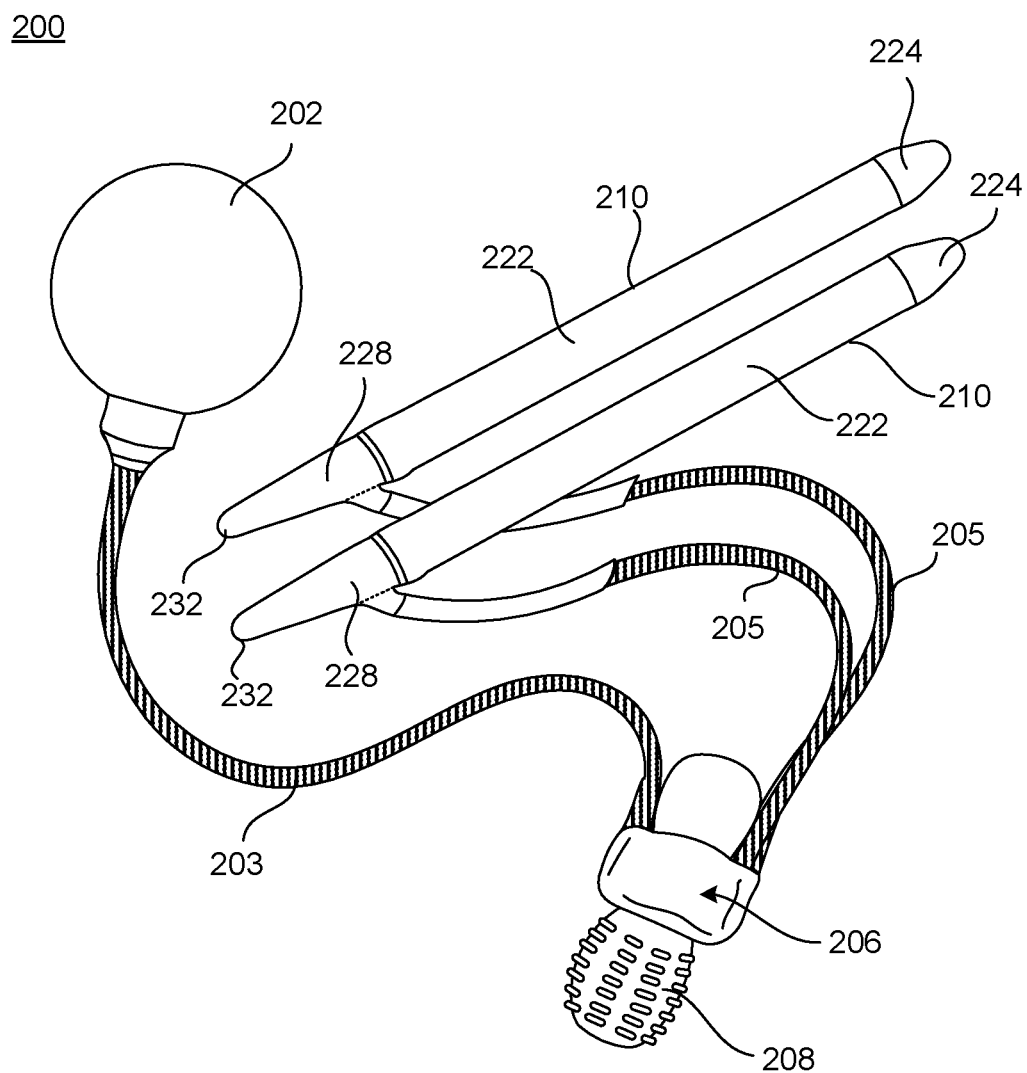
FIG. 2 illustrates an inflatable penile prosthesis according to an aspect.
Figure 3:
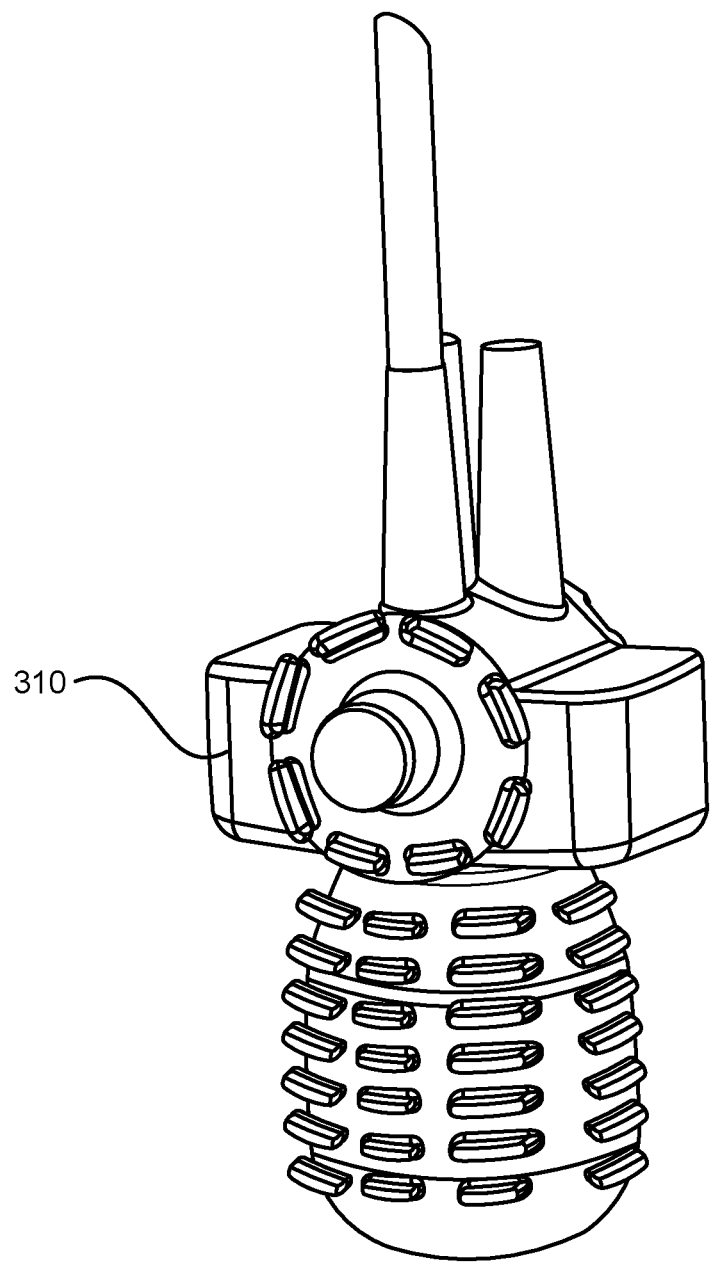
FIG. 3 is a perspective view of a portion of the penile prosthesis of FIG. 2.
Figure 4:
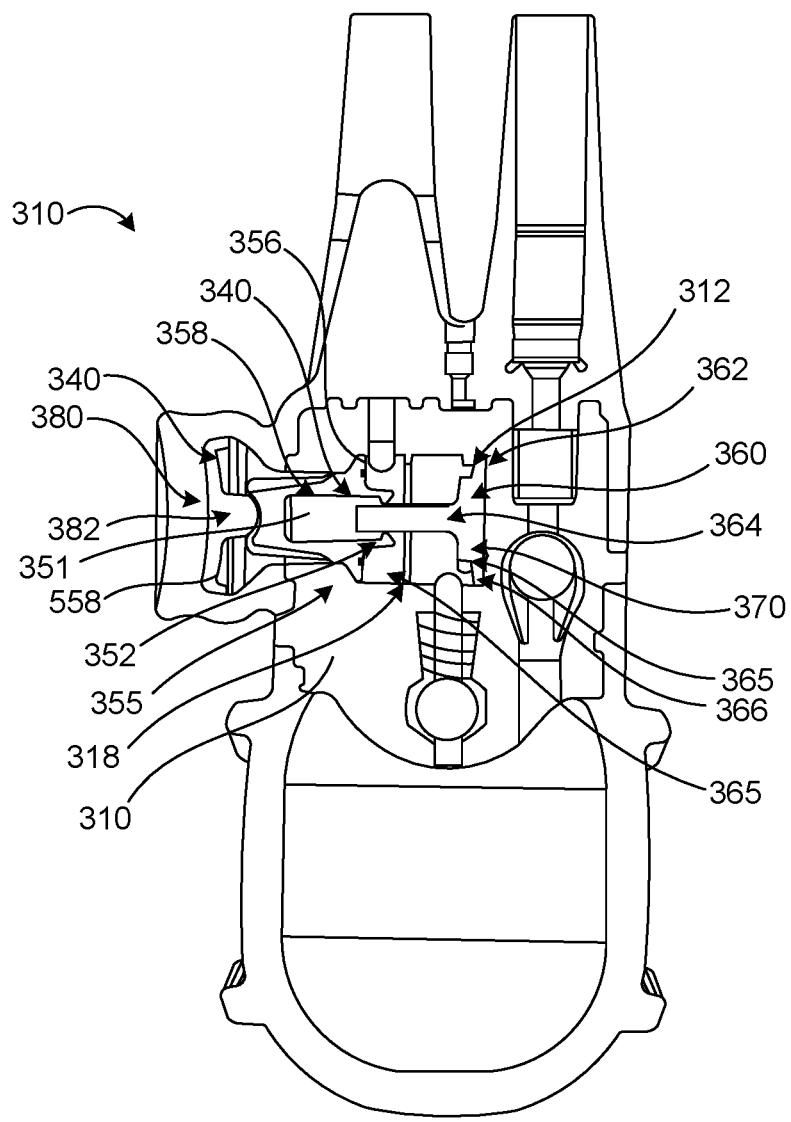
FIGS. 4-6 are cross-sectional views of a portion of the penile prosthesis of FIG. 2.

FIG. 2 illustrates an inflatable penile prosthesis 200 having a pump assembly 206 according to an aspect. The pump assembly 206 may include any of the features of the pump assemblies (including the push valve) described with reference to the previous figures. The penile prosthesis 200 may include a pair of inflatable cylinders 210, and the inflatable cylinders 210 are configured to be implanted in a penis. For example, one of the inflatable cylinders 210 may be disposed on one side of the penis, and the other inflatable cylinder 210 may be disposed on the other side of the penis. Each inflatable cylinder 210 may include a first end portion 224, a cavity or inflation chamber 222, and a second end portion 228 having a rear tip 232.

The pump assembly 206 may be implanted into the patient's scrotum. A pair of conduit connectors 205 may attach the pump assembly 206 to the inflatable cylinders 210 such that the pump assembly 206 is in fluid communication with the inflatable cylinders 210. Also, the pump assembly 206 may be in fluid communication with a fluid reservoir 202 via a conduit connector 203. The fluid reservoir 202 may be implanted into the user's abdomen. The inflation chamber or portion 222 of the inflatable cylinder 210 may be disposed within the penis. The first end portion 224 of the inflatable cylinder 210 may be at least partially disposed within the crown portion of the penis. The second end portion 228 may be implanted into the patient's pubic region PR with the rear tip 232 proximate the pubic bone PB.

In order to implant the inflatable cylinders 210, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the inflatable cylinders 210. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 228. The surgeon may measure the length of the corpora cavernosae from the incision and the dilated region of the pubic area to determine an appropriate size of the inflatable cylinders 210 to implant.

After the patient is prepared, the penile prosthesis 200 is implanted into the patient. The tip of the first end portion 824 of each inflatable cylinder 210 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 210 into the corpus cavernosum. This is done for each inflatable cylinder 210 of the pair. Once the inflation chamber 222 is in place, the surgeon may remove the suture from the tip. The surgeon then inserts the second end portion 228. The surgeon inserts the rear end of the inflatable cylinder 210 into the incision and forces the second end portion 228 toward the pubic bone PB until each inflatable cylinder 210 is in place.

A pump bulb 208 of the pump assembly 206 may be squeezed or depressed by the user in order to facilitate the transfer of fluid from the fluid reservoir 202 to the inflatable cylinders 210. For example, in the inflation mode, while the user is operating the pump bulb 208, the pump bulb 208 may receive the fluid from the fluid reservoir 802, and then output the fluid to the inflatable cylinders 210. When the user switches to the deflation mode, at least some of the fluid can automatically be transferred back to the fluid reservoir 202 (due to the difference in pressure from the inflatable cylinders 210 to the fluid reservoir 202). Then, the user may squeeze the inflatable cylinders 210 to facilitate the further transfer of fluid through the pump bulb 208 to the fluid reservoir 202.

Figure 5:
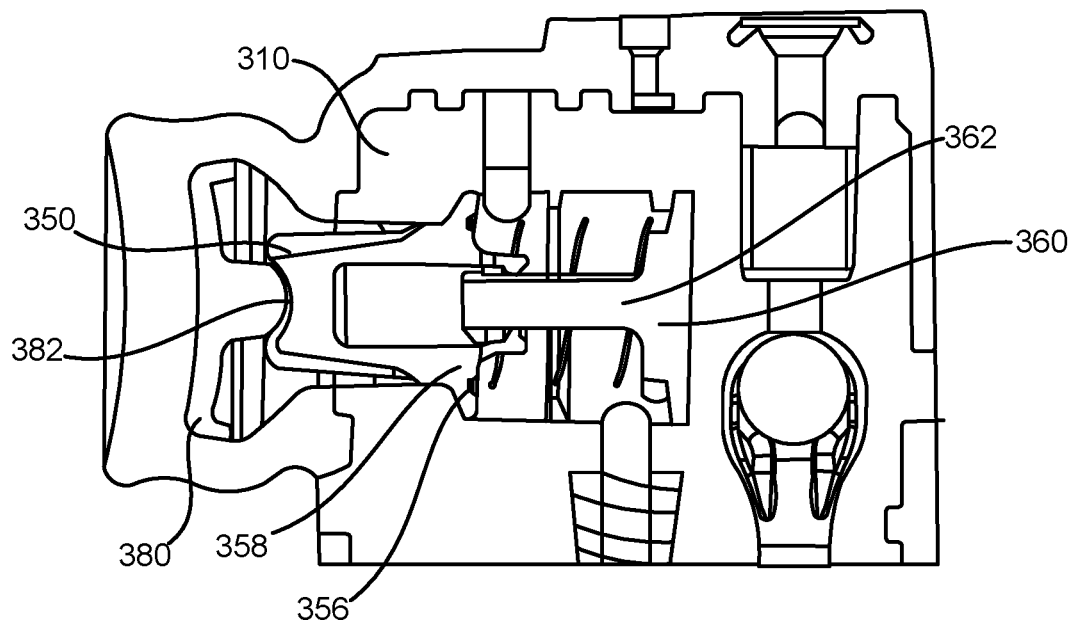
Figure 6:
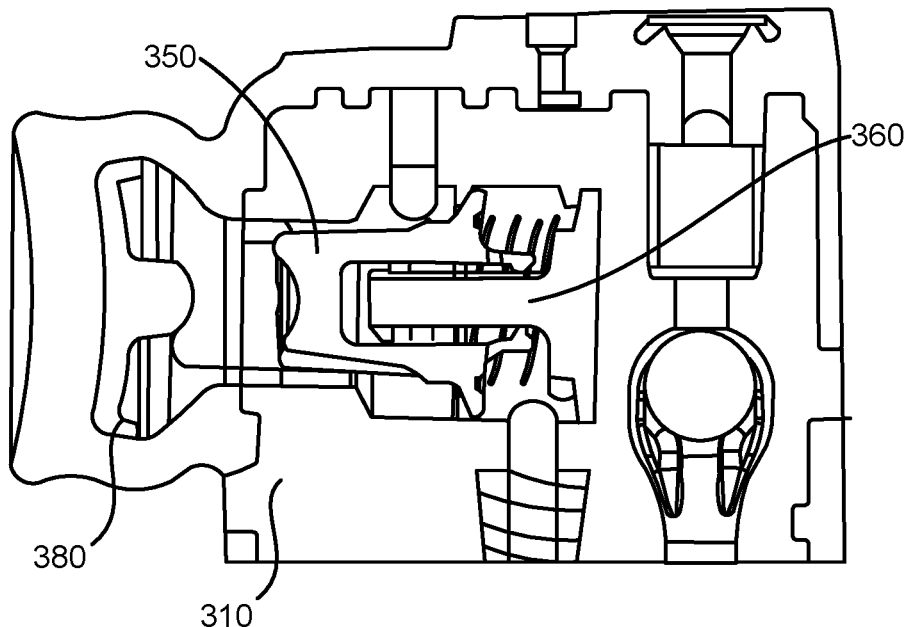

FIGS. 3-6 illustrate a valve body 310 according to an embodiment of the invention. FIG. 5 is a cross-sectional view of the valve body 310 with the valve or the movable valve element 340 in an inflate position or inflate mode. FIG. 6 is a cross-sectional view of the valve body 310 with the valve or the movable valve element 340 in a deflate position or mode.

In the illustrated embodiment, the valve or movable valve element 340 includes multiple members or pieces. The valve or movable valve element 340 includes a first member 350 and a second member 360. The first member 350 is configured to move with respect to the second member 360.

The second member 360 is fixedly coupled to the valve body 310. In some embodiments, the second member 360 is fixedly coupled to the valve body 310 via a mechanical or frictional coupling. In the illustrated embodiment, the second member 360 includes a surface 362 that is configured to engage retainment members or a retainment ring 312 of the valve body 310. In other embodiments, the second member 360 is fixedly coupled to the valve body 310 via an adhesive or other coupling method.

The second member 360 includes a projection 364. The projection 364 extends from a base portion of the second member 360 and is configured to be received by and at least partially disposed within a cavity 351 defined by the first member 350. The first member 350 includes a surface or ring 352 that is configured to engage the outer surface 365 of the projection 364. Accordingly, as the first member 350 moves with respect to the second member 360 (for example from an inflate position as shown in FIG. 5 to a deflate position as shown in FIG. 6), the surface or ring 352 slides along the outer surface 365 of the projection 364. In some embodiments, the outer surface of the projection is tapered or includes a tapered portion.

A biasing member 370 is disposed between the first member 350 and the second member 360. The biasing member 370 is configured to bias the first member 350 to the inflate position or mode. In the illustrated embodiment, the biasing member 370 is a spring member. In other embodiments, the biasing member is a different type of biasing member. In the illustrated embodiment, the first member 350 includes a spring retainer or groove 355 that is configured to receive and retain the spring 370. Similarly, the second member 360 includes a retainer or groove 366 that is configured to receive and retain the spring 370.

The first member 350 includes a surface 356 that is configured to engage a seal ring or member 318 defined by the valve housing 310. The engagement of the surface 356 and the seal ring or member 318 forms a fluidic seal.

In the illustrated embodiment, the movable valve element 440 includes a third member 380. The third member 380 includes a surface 382. In the illustrated embodiment, the surface is curved or non-planar. In the illustrated embodiment, the surface 382 is convex. The surface 382 is configured to contact or engage a surface 358 of the first member 350. The engagement of the surface 382 and the surface 358 facilitates the movement of the first member 350 from the inflate position to the deflate position (for example, when a user engages or presses the third member 380). In the illustrated embodiment, the engagement surface 358 of the first member 350 is curved or non-planar. In the illustrated embodiment, the surface 358 is has a convex shape.

Figure 7:
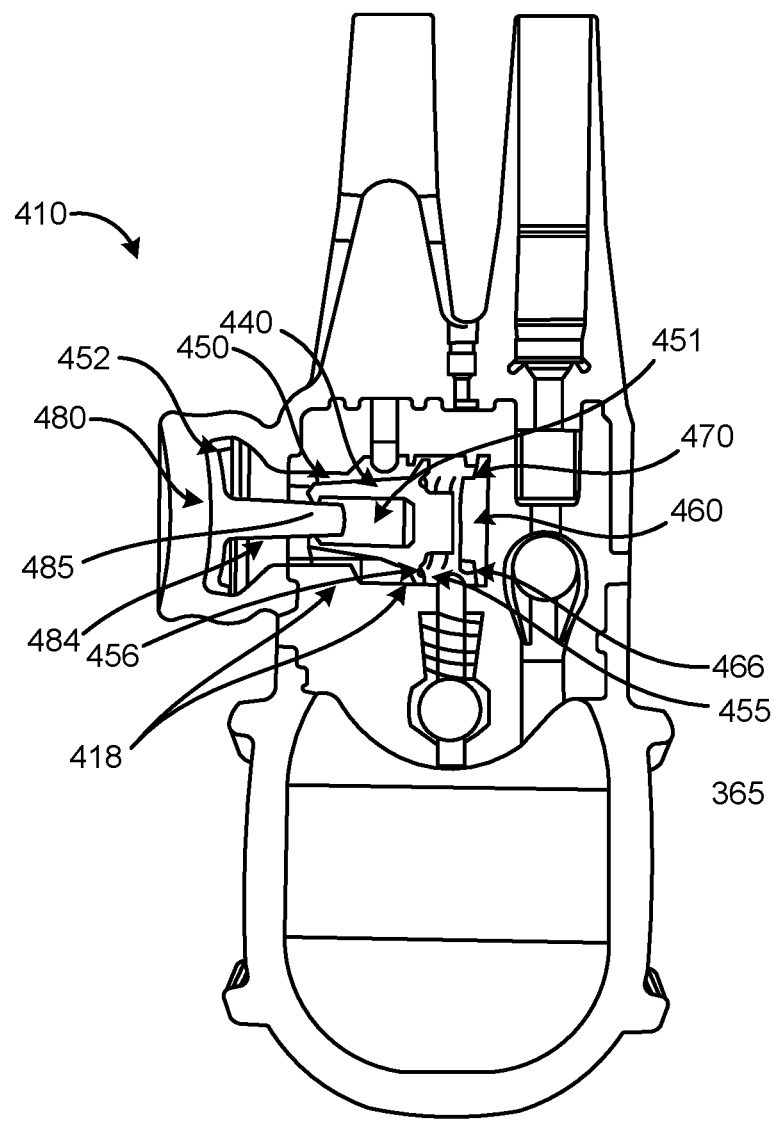
FIGS. 7-9 are cross-sectional views of a portion of a penile prosthesis according to an aspect.
Figure 8:
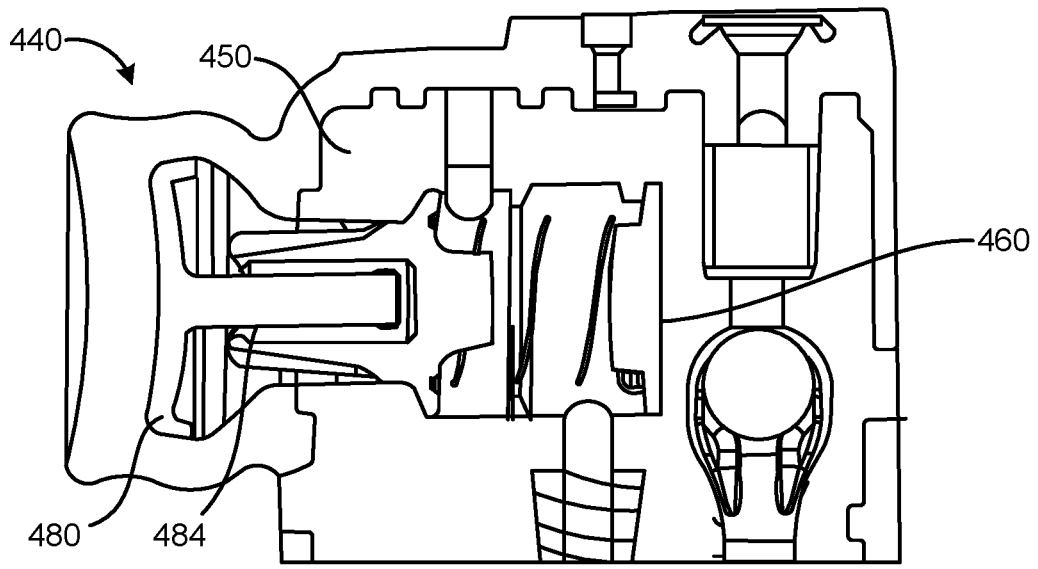
Figure 9:
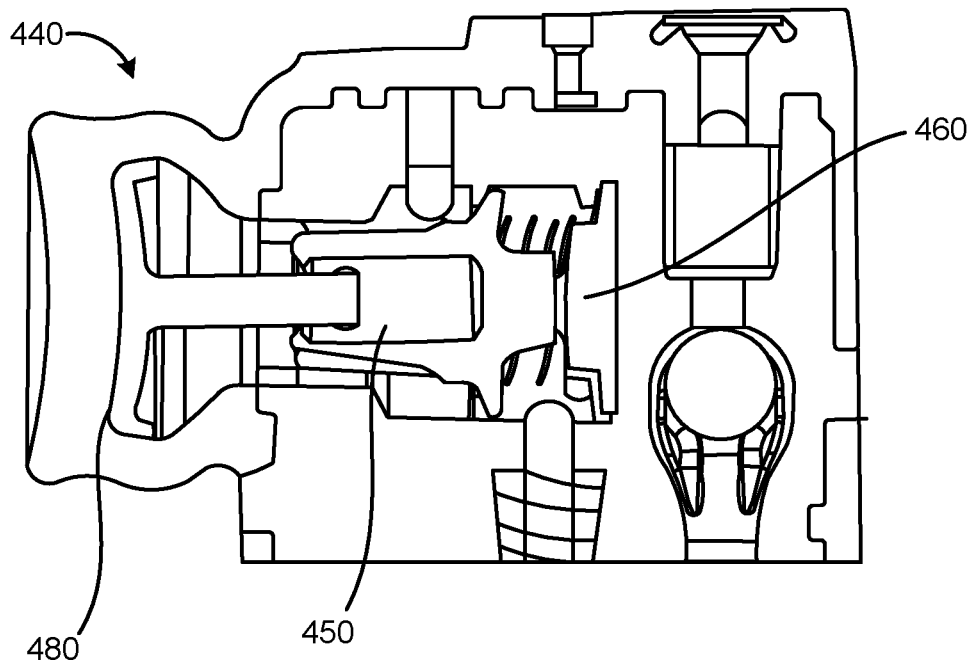

FIGS. 7-9 illustrate a valve body 410 according to an embodiment of the invention. FIG. 8 is a cross-sectional view of the valve body 410 with the valve or the movable valve element 440 in an inflate position or inflate mode. FIG. 9 is a cross-sectional view of the valve body 410 with the valve or the movable valve element 440 in a deflate position or mode.

In the illustrated embodiment, the valve or movable valve element 440 includes multiple members or pieces. The valve or movable valve element 440 includes a first member 450 and a second member 460. The first member 450 is configured to move with respect to the second member 460.

The second member 460 is fixedly coupled to the valve body 410. In some embodiments, the second member 460 is fixedly coupled to the valve body 410 via a mechanical or frictional coupling. In the illustrated embodiment, the second member 460 includes a surface 462 that is configured to engage retainment members or a retainment ring 412 of the valve body 410. In other embodiments, the second member 460 is fixedly coupled to the valve body 410 via an adhesive or other coupling method.

A biasing member 470 is disposed between the first member 350 and the second member 460. The biasing member 470 is configured to bias the first member 450 to the inflate position or mode. In the illustrated embodiment, the biasing member 470 is a spring member. In other embodiments, the biasing member is a different type of biasing member. In the illustrated embodiment, the first member 450 includes a spring retainer or groove 455 that is configured to receive and retain the spring 470. Similarly, the second member 460 includes a retainer or groove 466 that is configured to receive and retain the spring 470.

The first member 450 includes a surface 456 that is configured to engage a seal ring or member 418 defined by the valve housing 410. The engagement of the surface 456 and the seal ring or member 418 forms a fluidic seal.

In the illustrated embodiment, the movable valve element 440 includes a third member 480. The third member 480 includes a projection 484. The projection 484 extends from a base portion of the third member 480 and is configured to be received by and at least partially disposed within a cavity 451 defined by the first member 450. The first member 450 includes a surface or ring 452 that is configured to engage the outer surface 485 of the projection 484. Accordingly, as the first member 450 moves with respect to the third member 480 (for example from an inflate position as shown in FIG. 8 to a deflate position as shown in FIG. 9), the surface or ring 452 slides along the outer surface 485 of the projection 484. In some embodiments, the outer surface of the projection is tapered or includes a tapered portion.

Figure 10:
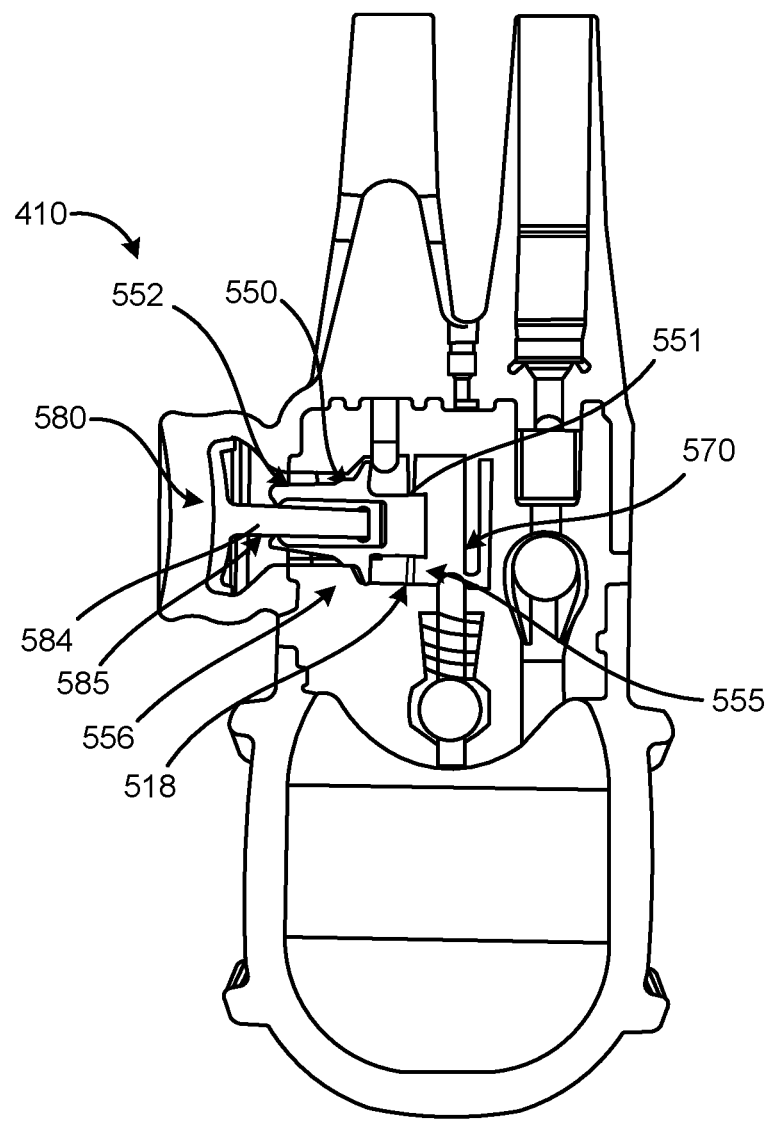
FIGS. 10-12 are cross-sectional views of a portion of a penile prosthesis according to an aspect.
Figure 11:
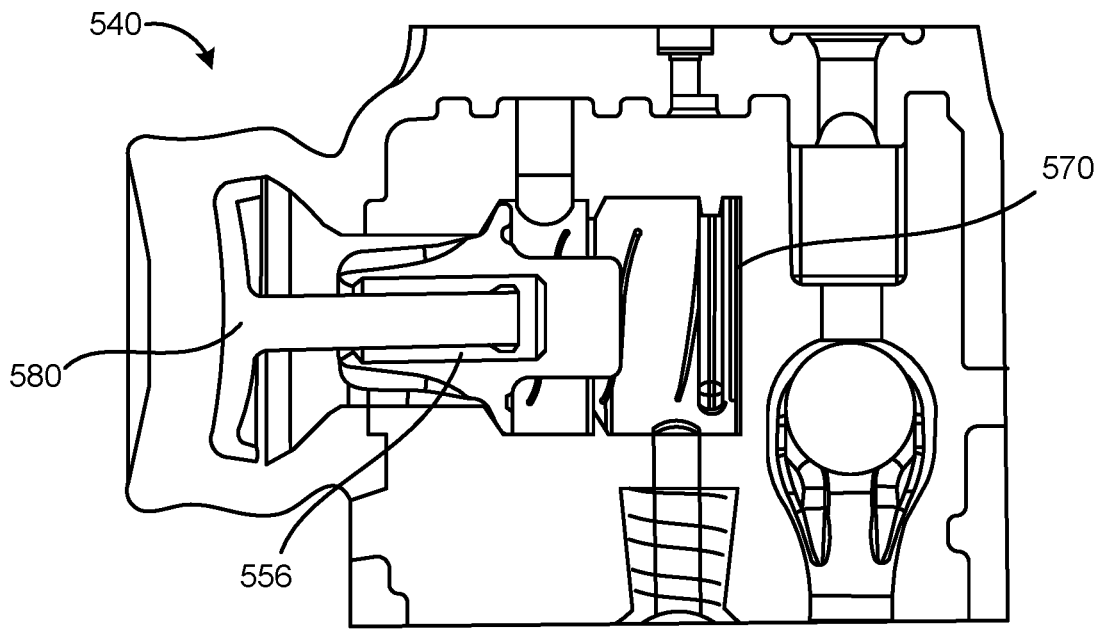
Figure 12:
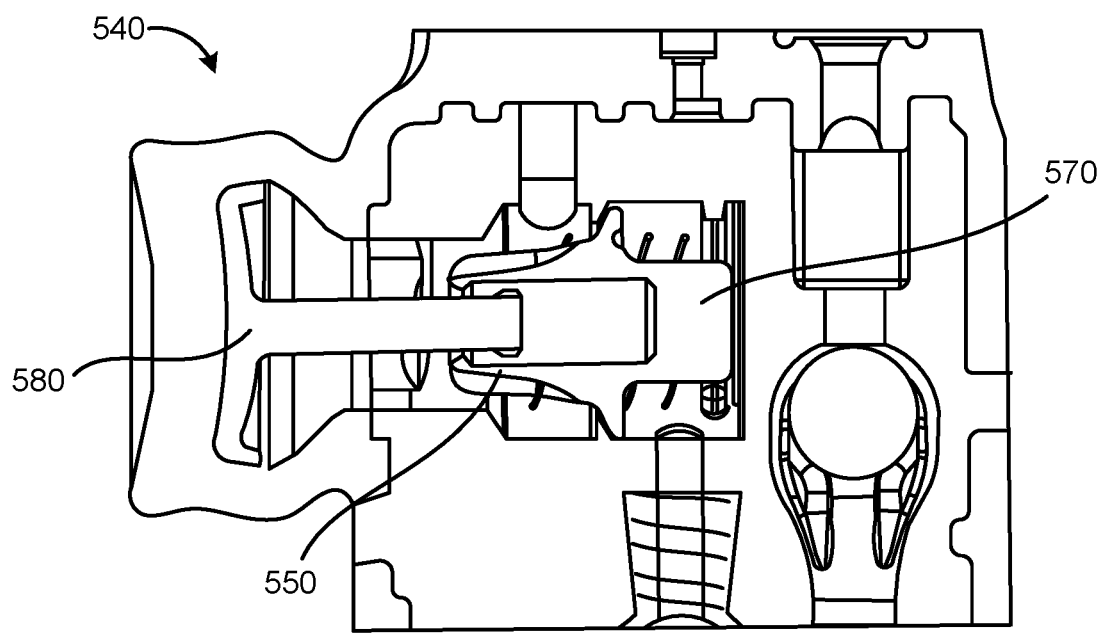

FIGS. 10-12 illustrate a valve body 510 according to an embodiment of the invention. FIG. 11 is a cross-sectional view of the valve body 510 with the valve or the movable valve element 540 in an inflate position or inflate mode. FIG. 12 is a cross-sectional view of the valve body 510 with the valve or the movable valve element 540 in a deflate position or mode.

In the illustrated embodiment, the valve or movable valve element 540 includes multiple members or pieces. The valve or movable valve element 540 includes a first member 550 and a second member 580. The first member 550 is configured to move with respect to the second member 580.

A biasing member 570 is disposed between the first member 550 and the valve body 510. The biasing member 570 is configured to bias the first member 550 to the inflate position or mode. In the illustrated embodiment, the biasing member 570 is a spring member. In other embodiments, the biasing member is a different type of biasing member. In the illustrated embodiment, the first member 550 includes a spring retainer or groove 555 that is configured to receive and retain the spring 570.

The first member 550 includes a surface 556 that is configured to engage a seal ring or member 518 defined by the valve housing 510. The engagement of the surface 556 and the seal ring or member 518 forms a fluidic seal.

In the illustrated embodiment, the movable valve element 540 includes a second member 580. The second member 580 includes a projection 584. The projection 584 extends from a base portion of the second member 580 and is configured to be received by and at least partially disposed within a cavity 551 defined by the first member 550. The first member 550 includes a surface or ring 552 that is configured to engage the outer surface 585 of the projection 584. Accordingly, as the first member 550 moves with respect to the second member 580 (for example from an inflate position as shown in FIG. 11 to a deflate position as shown in FIG. 12), the surface or ring 552 slides along the outer surface 585 of the projection 584. In some embodiments, the outer surface of the projection is tapered or includes a tapered portion.

Figure 13:
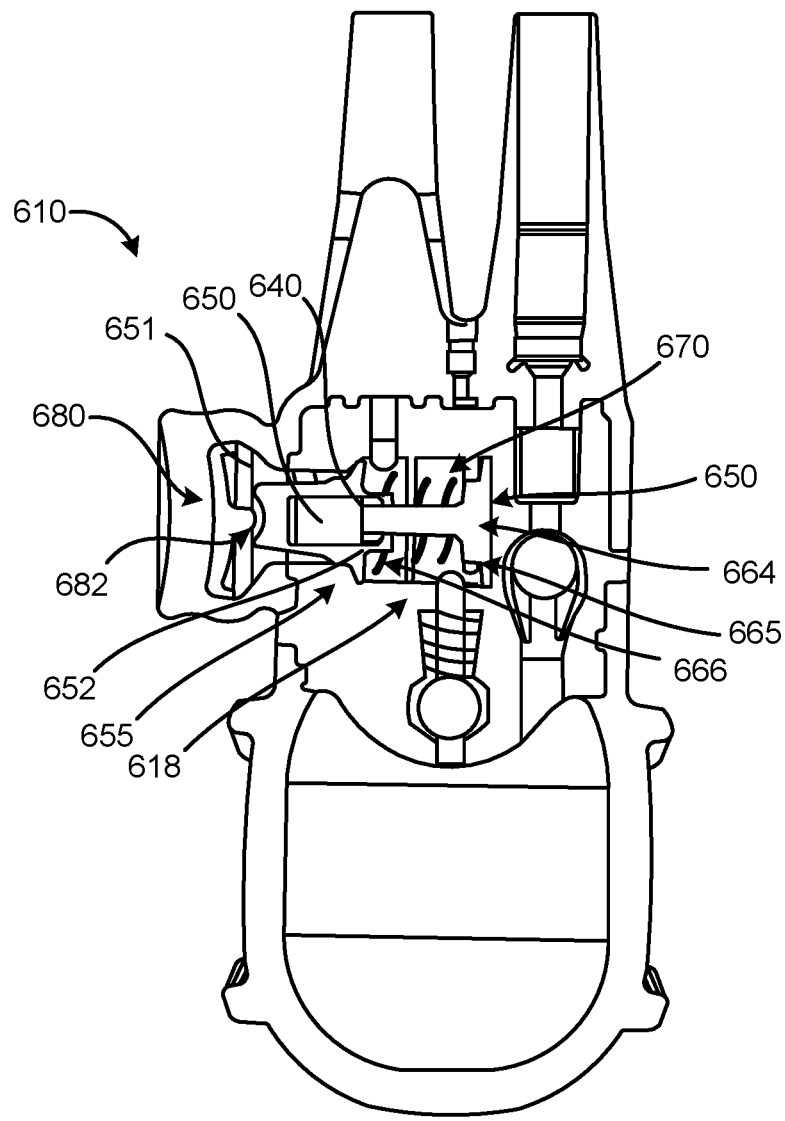
FIGS. 13-15 are cross-sectional views of a portion of a penile prosthesis according to an aspect.
Figure 14:
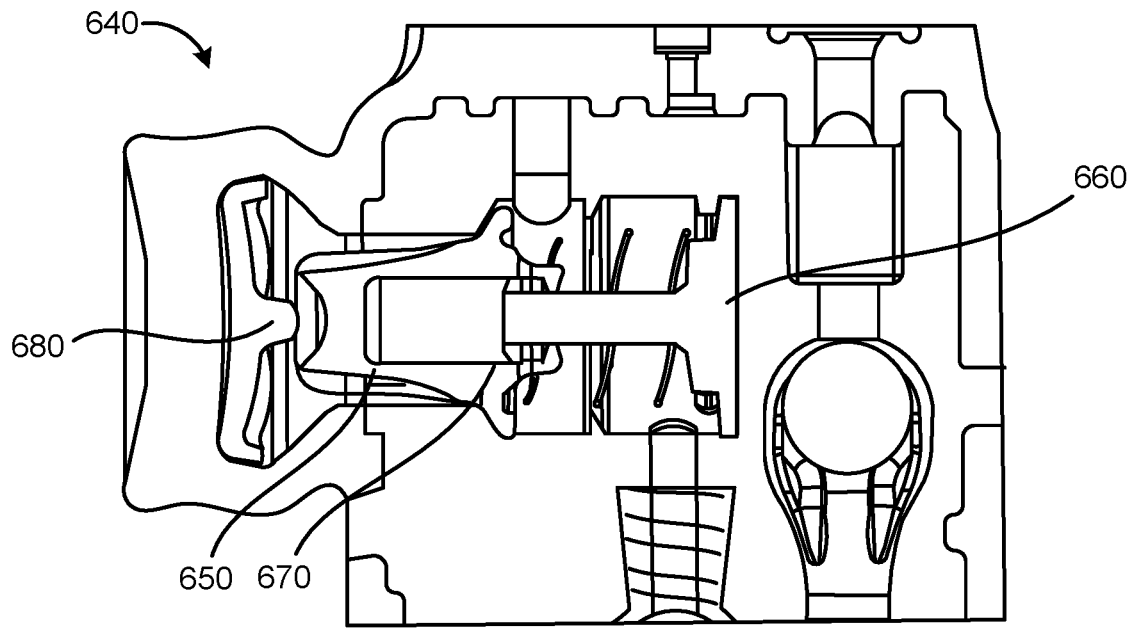
Figure 15:
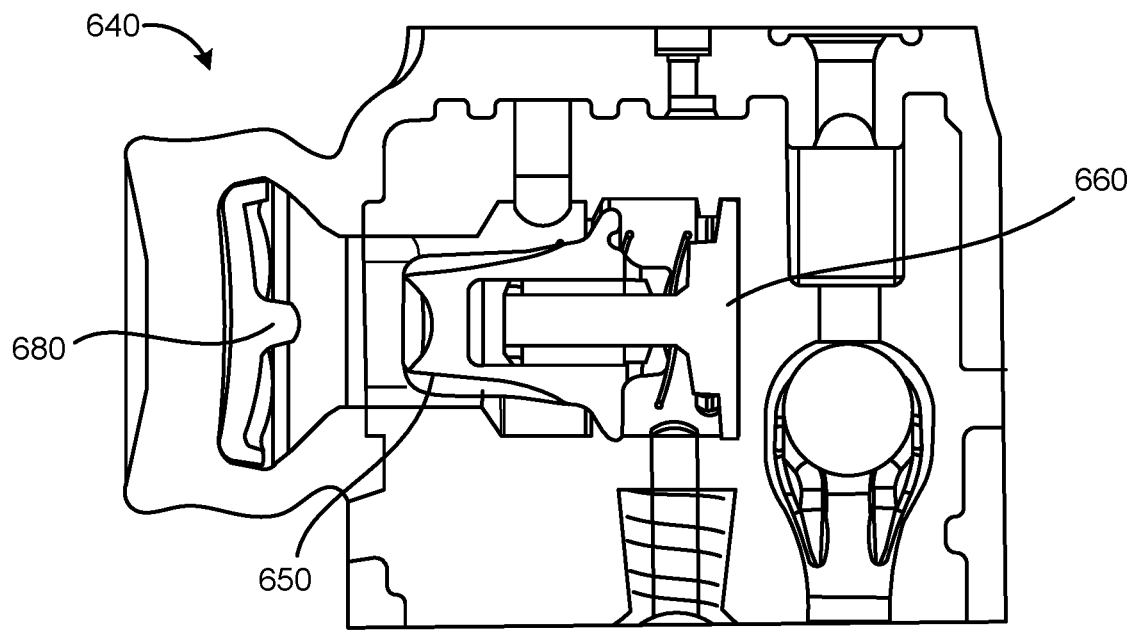

FIGS. 13-15 illustrate a valve body 610 according to an embodiment of the invention. FIG. 14 is a cross-sectional view of the valve body 610 with the valve or the movable valve element 640 in an inflate position or inflate mode. FIG. 15 is a cross-sectional view of the valve body 610 with the valve or the movable valve element 640 in a deflate position or mode.

In the illustrated embodiment, the valve or movable valve element 640 includes multiple members or pieces. The valve or movable valve element 640 includes a first member 650 and a second member 660. The first member 650 is configured to move with respect to the second member 660.

The second member 660 is fixedly coupled to the valve body 610. In some embodiments, the second member 660 is fixedly coupled to the valve body 610 via a mechanical or frictional coupling. In the illustrated embodiment, the second member 660 includes a surface 662 that is configured to engage retainment members or a retainment ring 612 of the valve body 610. In other embodiments, the second member 660 is fixedly coupled to the valve body 610 via an adhesive or other coupling method.

The second member 660 includes a projection 664. The projection 664 extends from a base portion of the second member 660 and is configured to be received by and at least partially disposed within a cavity 651 defined by the first member 650. The first member 650 includes a surface or ring 652 that is configured to engage the outer surface 665 of the projection 664. Accordingly, as the first member 650 moves with respect to the second member 660 (for example from an inflate position as shown in FIG. 14 to a deflate position as shown in FIG. 15), the surface or ring 652 slides along the outer surface 665 of the projection 664. In some embodiments, the outer surface of the projection is tapered or includes a tapered portion.

A biasing member 670 is disposed between the first member 650 and the second member 660. The biasing member 670 is configured to bias the first member 650 to the inflate position or mode. In the illustrated embodiment, the biasing member 670 is a spring member. In other embodiments, the biasing member is a different type of biasing member. In the illustrated embodiment, the first member 650 includes a spring retainer or groove 655 that is configured to receive and retain the spring 670. Similarly, the second member 660 includes a retainer or groove 666 that is configured to receive and retain the spring 670.

The first member 650 includes a surface 656 that is configured to engage a seal ring or member 618 defined by the valve housing 610. The engagement of the surface 656 and the seal ring or member 618 forms a fluidic seal.

In the illustrated embodiment, the movable valve element 640 includes a third member 680. The third member 680 includes a surface 682. In the illustrated embodiment, the surface is curved or non-planar. In the illustrated embodiment, the surface 682 is convex. The surface 682 is configured to contact or engage a surface 658 of the first member 650. The engagement of the surface 682 and the surface 658 facilitate the movement of the first member 650 from the inflate position to the deflate position (for example, when a user engages or presses the third member 680). In the illustrated embodiment, the engagement surface 658 of the first member 650 is curved or non-planar. In the illustrated embodiment, the surface 658 is has a convex shape.

Figure 16:
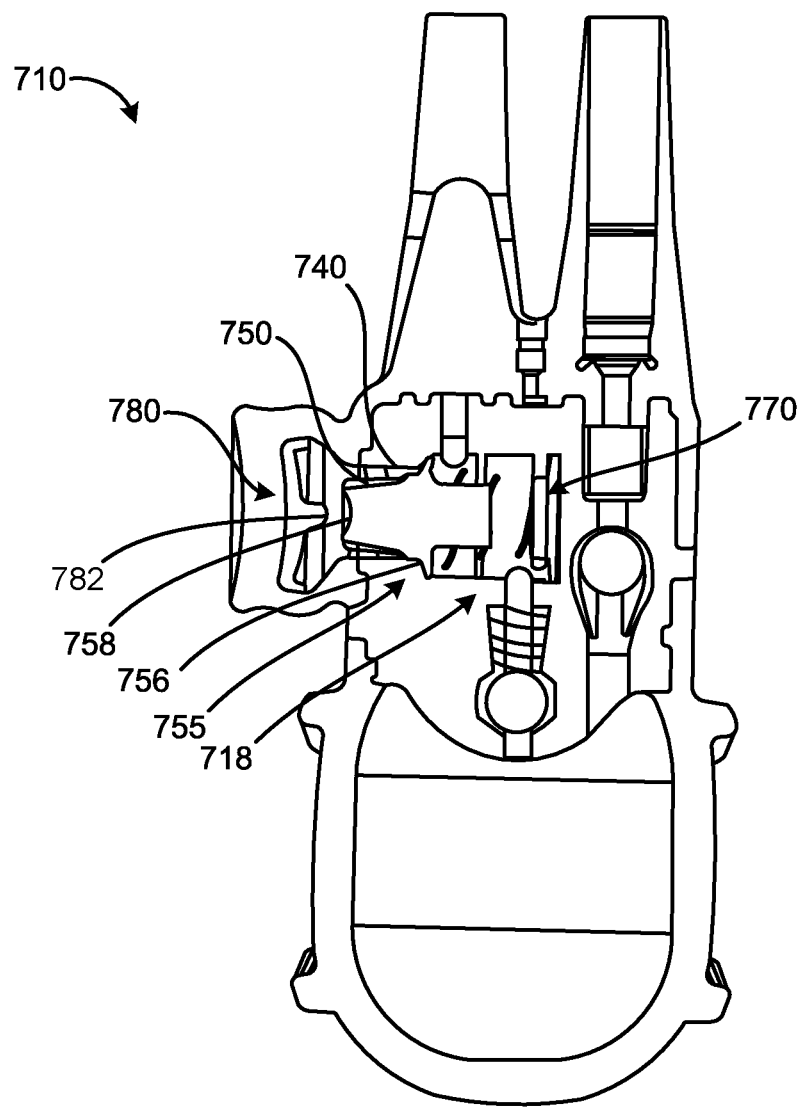
FIGS. 16-18 are cross-sectional views of a portion of a penile prosthesis according to an aspect.
Figure 17:
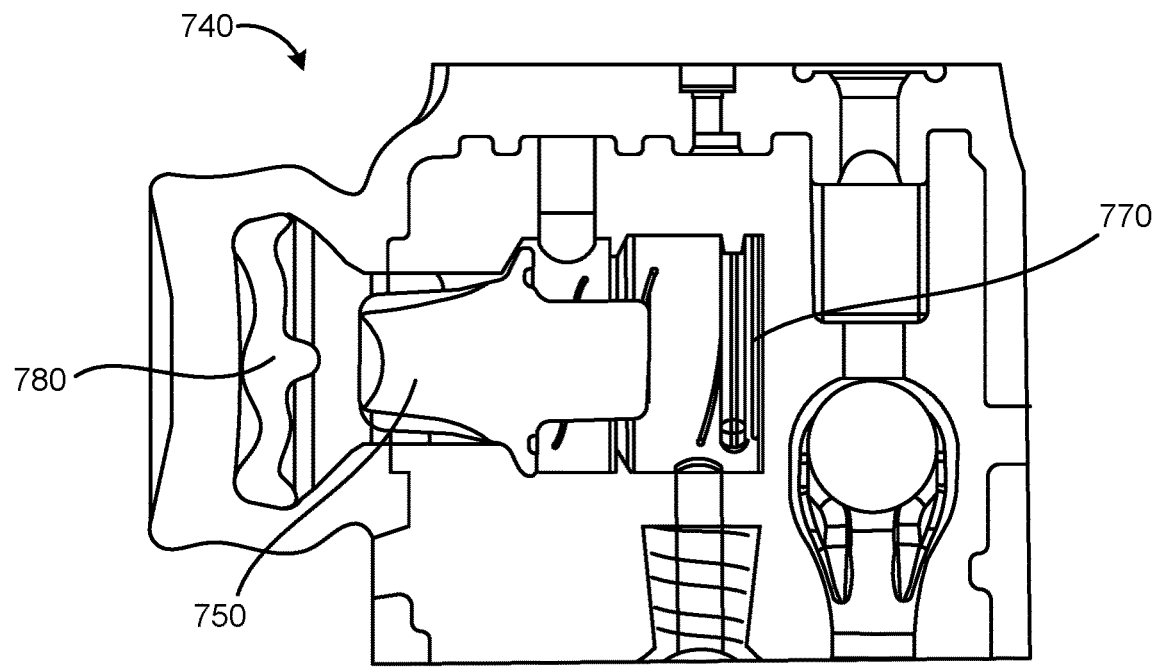
Figure 18:
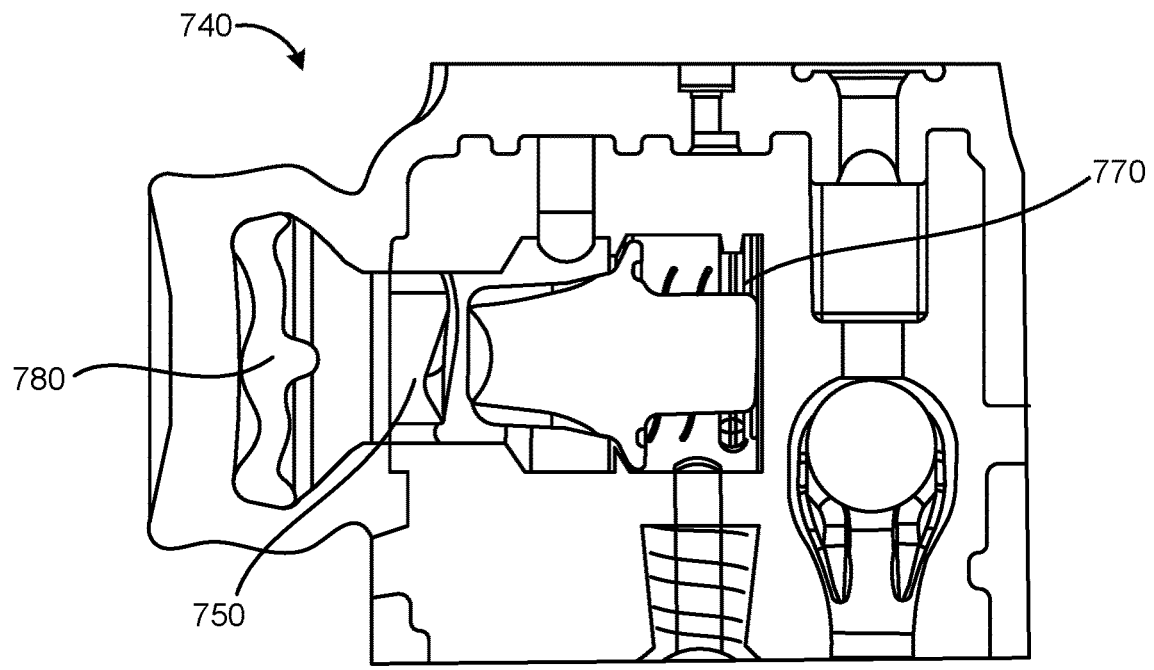

FIGS. 16-18 illustrate a valve body 710 according to an embodiment of the invention. FIG. 17 is a cross-sectional view of the valve body 710 with the valve or the movable valve element 740 in an inflate position or inflate mode. FIG. 18 is a cross-sectional view of the valve body 710 with the valve or the movable valve element 740 in a deflate position or mode.

In the illustrated embodiment, the valve or movable valve element 740 includes multiple members or pieces. The valve or movable valve element 740 includes a first member 750 and a second member 780. The first member 750 is configured to move with respect to the second member 780.

A biasing member 770 is disposed between the first member 750 and the valve body 710. The biasing member 770 is configured to bias the first member 750 to the inflate position or mode. In the illustrated embodiment, the biasing member 770 is a spring member. In other embodiments, the biasing member is a different type of biasing member. In the illustrated embodiment, the first member 750 includes a spring retainer or groove 755 that is configured to receive and retain the spring 770.

The first member 750 includes a surface 756 that is configured to engage a seal ring or member 718 defined by the valve housing 710. The engagement of the surface 756 and the seal ring or member 718 forms a fluidic seal.

In the illustrated embodiment, the movable valve element 740 includes a second member 780. The second member 780 includes a surface 782. In the illustrated embodiment, the surface is curved or non-planar. In the illustrated embodiment, the surface 782 is convex. The surface 782 is configured to contact or engage a surface 758 of the first member 750. The engagement of the surface 782 and the surface 758 facilitates the movement of the first member 750 from the inflate position to the deflate position (for example, when a user engages or presses the second member 780). In the illustrated embodiment, the engagement surface 758 of the first member 750 is curved or non-planar. In the illustrated embodiment, the surface 758 is has a convex shape.

Figure 19:
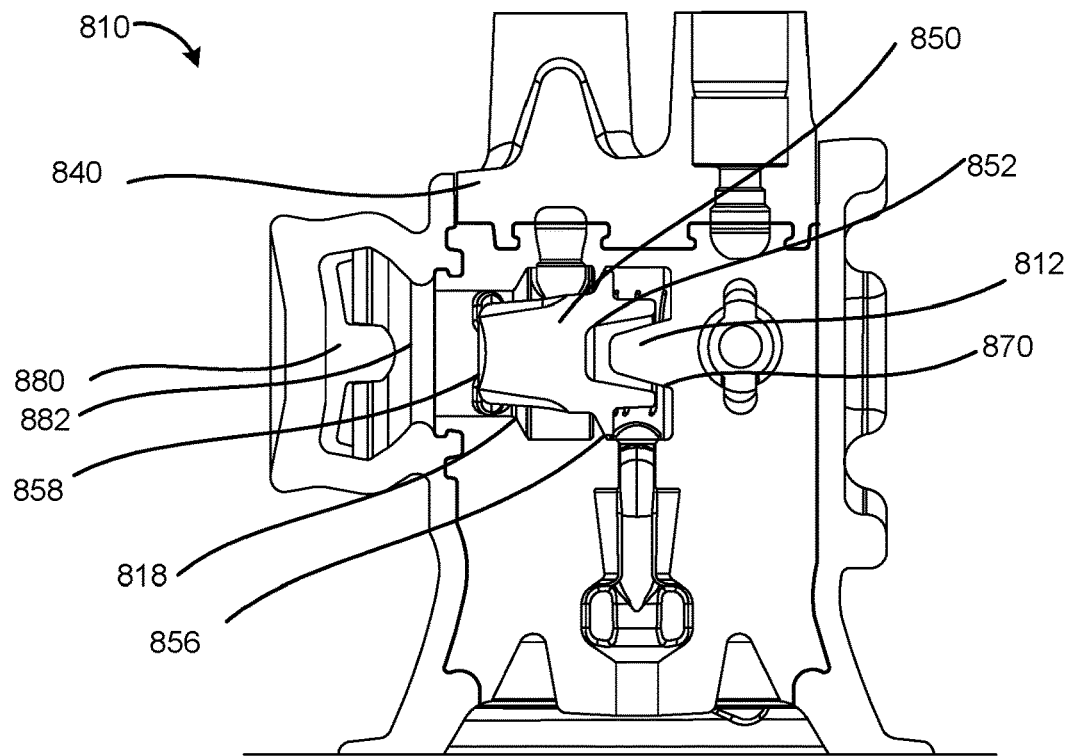
FIGS. 19-20 are cross-sectional views of a portion of a penile prosthesis according to an aspect.
Figure 20:
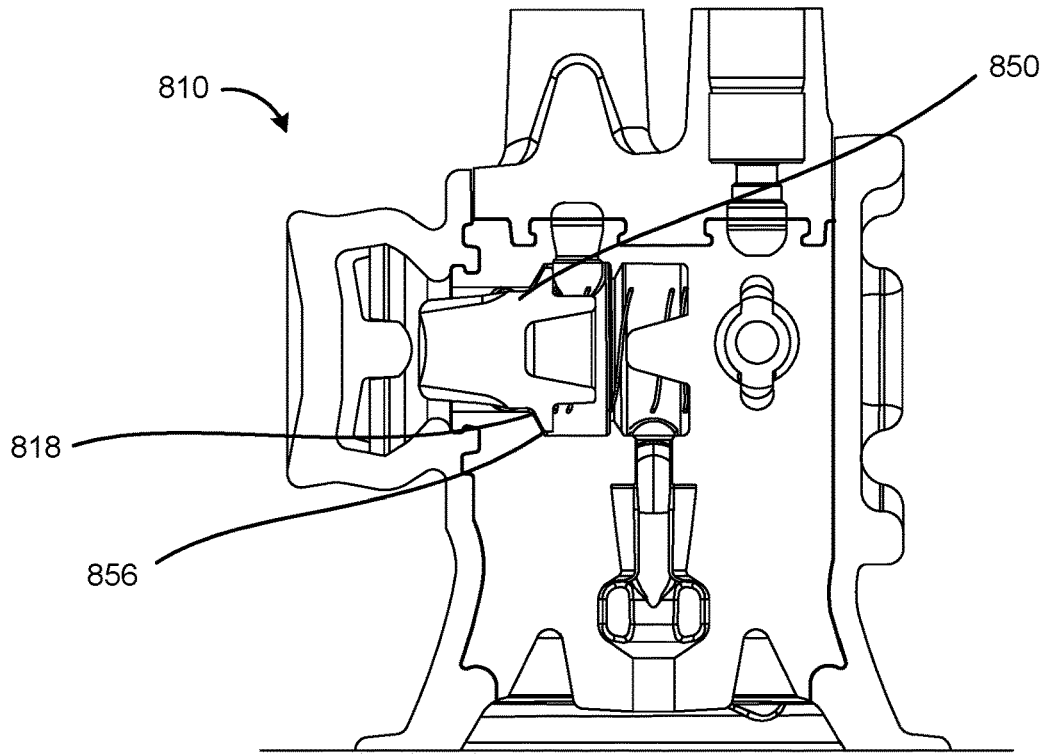

FIGS. 19-20 illustrate a valve body 810 according to an embodiment of the invention. FIG. 19 is a cross-sectional view of the valve body 810 with the valve or the movable valve element 840 in an inflate position or inflate mode. FIG. 19 is a cross-sectional view of the valve body 810 with the valve or the movable valve element 840 in a deflate position or mode.

In the illustrated embodiment, the valve or movable valve element 840 includes multiple members or pieces. The valve or movable valve element 840 includes a first member 850 and a second member 880. The first member 850 is configured to move with respect to the second member 880.

A biasing member 870 is disposed between the first member 850 and the valve body 810. The biasing member 870 is configured to bias the first member 850 to the inflate position or mode. In the illustrated embodiment, the biasing member 870 is a spring member. In other embodiments, the biasing member is a different type of biasing member. In the illustrated embodiment, the first member 850 includes a spring retainer or groove that is configured to receive and retain the spring 870.

In the illustrated embodiment, the first member 850 defines a cavity 852 and the valve body 810 includes a projection portion 812. The cavity 852 is configured to receive the projection portion 812 of the valve body 810. For example, as best illustrated in FIG. 19, when the valve or movable valve element 840 is in the deflate position, the projection portion 812 is received or disposed within the cavity 852 of the first member 850. In some embodiments, the interaction or engagement of the projection portion 812 with the portion of the first member 850 that defines the cavity 852 may help maintain alignment of the first member 850 within the valve body 810. For example, in some embodiment, if the first member 850 becomes misaligned, the projection portion 812 may engage the first member 850 to realign the first member 850 within the valve body 810.

The first member 850 includes a surface 856 that is configured to engage a seal ring or member 818 defined by the valve housing 810. The engagement of the surface 856 and the seal ring or member 818 forms a fluidic seal. For example, in some embodiments and as best illustrated in FIG. 18, the surface 856 is configured to contact the seal ring or member 818 to form a fluidic seal when the first member 850 is in the inflate position.

In the illustrated embodiment, the movable valve element 840 includes a second member 880. The second member 880 includes a surface 882. In the illustrated embodiment, the surface is curved or non-planar. In the illustrated embodiment, the surface 882 is convex. The surface 882 is configured to contact or engage a surface 858 of the first member 850. The engagement of the surface 882 and the surface 858 facilitates the movement of the first member 850 from the inflate position to the deflate position (for example, when a user engages or presses the second member 880). In the illustrated embodiment, the surface 858 of the first member 850 is curved or non-planar. In the illustrated embodiment, the surface 858 is has a convex shape.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
   a fluid reservoir configured to hold fluid;
   an inflatable member; and
   a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, the valve body including a projection,
   wherein the valve includes a first member and second member, the first member being configured to move with respect to the second member, the first member of the valve defines a cavity, the cavity being configured to receive the projection when the valve is disposed in the deflation position.

2. The inflatable penile prosthesis of claim 1, wherein the second member of the valve configured to move within the valve body.

3. The inflatable penile prosthesis of claim 1, wherein the first member of the valve defines a cavity, the second member of the valve includes a projection, the cavity of the first member being configured to receive the projection of the second member.

4. The inflatable penile prosthesis of claim 1, wherein the second member of the valve is configured to engage the first member of the valve.

5. The inflatable penile prosthesis of claim 1, wherein the second member of the valve includes a surface configured to engage a surface of the first member of the valve, the surface of the second member being a curved surface, the surface of the first member being a curved surface.

6. The inflatable penile prosthesis of claim 1, wherein the second member of the valve includes a convex surface configured to engage a concave surface of the first member of the valve.

7. The inflatable penile prosthesis of claim 1, further comprising a biasing member disposed between the first member and the second member.

8. The inflatable penile prosthesis of claim 1, further comprising a spring member disposed between the first member and the second member.

9. The inflatable penile prosthesis of claim 1, wherein the valve body includes a sealing ring, the first member of the valve includes a surface, the surface being configured to engage the sealing ring when the valve is in the deflation position.

10. The inflatable penile prosthesis of claim 1, wherein the first member of the valve includes a contact ring, the second member of the valve includes a projection having an outer surface, the contact ring being configured to engage the outer surface of the projection.

11. The inflatable penile prosthesis of claim 1, wherein the valve body includes a retainer member configured to engage the second member of the valve to help fixedly couple the second member of the valve to the valve body.

12. An inflatable penile prosthesis comprising:
    a fluid reservoir configured to hold fluid;
    an inflatable member; and
    a pump assembly configured to transfer the fluid between the fluid reservoir and the inflatable member, the pump assembly including a pump bulb, a valve body, a valve disposed within the valve body, a first fluid port configured to be fluidly coupled to the fluid reservoir, and a second fluid port configured to be fluidly coupled to the inflatable member, the valve being configured to move between an inflation position and a deflation position, the valve body including a projection,
    wherein the valve includes a first member and second member, the first member being configured to move with respect to the second member, the first member of the valve defines a cavity, the cavity being configured to receive the projection when the valve is disposed in the deflation position, the valve member includes a biasing member disposed between a portion of the valve body and the first member of the valve.

13. The inflatable penile prosthesis of claim 12, wherein the biasing member is a spring.

14. The inflatable penile prosthesis of claim 12, wherein the first member of the valve includes a surface that is configured to engage a surface of the second member of the valve.

15. The inflatable penile prosthesis of claim 12, wherein the first member of the valve includes a convex surface that is configured to engage a surface of the second member of the valve.

16. The inflatable penile prosthesis of claim 12, wherein the valve body includes a sealing ring, the first member of the valve includes a surface, the surface being configured to engage the sealing ring when the valve is in the deflation position.

* * * * *